(12) United States Patent
Harren et al.

(10) Patent No.: US 7,625,957 B2
(45) Date of Patent: Dec. 1, 2009

(54) WATER-ABSORBING POLYMER PARTICLES DELAYING THE DECOMPOSITION OF BODY FLUIDS, COMPOSITES COMPRISING THESE AND USE THEREOF

(75) Inventors: Jörg Harren, Krefeld (DE); Jörg Issberner, Willich-Neersen (DE); Harald Schmidt, Tonisvorst (DE)

(73) Assignee: Stockhausen GmbH, Krefeld (DE)

( * ) Notice: Subject to any disclaimer, the term of this patent is extended or adjusted under 35 U.S.C. 154(b) by 517 days.

(21) Appl. No.: 10/512,351

(22) PCT Filed: Apr. 23, 2003

(86) PCT No.: PCT/EP03/04203

§ 371 (c)(1),
(2), (4) Date: Apr. 4, 2005

(87) PCT Pub. No.: WO03/090799

PCT Pub. Date: Nov. 6, 2003

(65) Prior Publication Data

US 2005/0171235 A1    Aug. 4, 2005

(30) Foreign Application Priority Data

Apr. 23, 2002 (DE) ............................. 102 18 147

(51) Int. Cl.
*C08K 3/10* (2006.01)
(52) U.S. Cl. ............................... 523/122; 524/403
(58) Field of Classification Search ................. 523/122; 524/403
See application file for complete search history.

(56) References Cited

U.S. PATENT DOCUMENTS

| | | | |
|---|---|---|---|
| 4,728,323 A | 3/1988 | Matson | |
| 5,149,334 A * | 9/1992 | Lahrman et al. | 604/367 |
| 5,468,811 A * | 11/1995 | Moro et al. | 525/263 |
| 5,662,913 A | 9/1997 | Capelli | |
| 6,277,772 B1 * | 8/2001 | Gancet et al. | 442/327 |
| 2002/0082340 A1 | 6/2002 | Hanke et al. | |
| 2002/0122832 A1 | 9/2002 | Hanke et al. | |
| 2004/0138362 A1 | 7/2004 | Kim | |

FOREIGN PATENT DOCUMENTS

| | | |
|---|---|---|
| DE | 198 13 443 A1 | 10/1998 |
| EP | 0 255 248 A2 | 2/1988 |
| WO | WO 00/78281 A1 | 12/2000 |
| WO | WO 01/41819 A1 | 6/2001 |
| WO | 03002164 A2 | 1/2003 |
| WO | WO 03/002164 A2 | 1/2003 |
| WO | WO 03/002618 A1 | 1/2003 |
| WO | WO 03/090799 A1 | 11/2003 |

OTHER PUBLICATIONS

International Preliminary Examination Report (IPER) mailed on Dec. 9, 2004 in PCT/EP2003/004203.

* cited by examiner

*Primary Examiner*—Kriellion A Sanders
(74) *Attorney, Agent, or Firm*—Smith Moore Leatherwood LLP

(57) ABSTRACT

Water-absorbing, antimicrobial polymer particles comprising from about 1 to about 500 ppm, based on the particles, of a silver ion based on a silver salt, wherein the silver salt has a solubility product of at least about $1\times10^{-8}$ $(mol/l)^{m+n}$; at least about 10 wt. %, based on the polymer particle, of a water-absorbing polymer based on: ($\alpha 1$) from about 50 to about 99.99 wt. % polymerized, ethylenically unsaturated, acid groups-containing monomers or salts thereof, ($\alpha 2$) 0 to about 40 wt. % polymerized, mono-ethylenically unsaturated monomers polymerizable with $\alpha 1$, ($\alpha 3$) from about 0.01 to about 5 wt. %, preferably from about 0.1 to about 3 wt. % of one or more crosslinkers, ($\alpha 4$) 0 to about 30 wt. % of a water soluble polymer and ($\alpha 5$) 0 to about 20 wt. % of auxiliaries, the concentration of the silver ion based on a silver salt in at most about 90 vol. % of the particles is less than about 0.01 ppm.

13 Claims, No Drawings

WATER-ABSORBING POLYMER PARTICLES DELAYING THE DECOMPOSITION OF BODY FLUIDS, COMPOSITES COMPRISING THESE AND USE THEREOF

This application is a national stage application under 35 U.S.C. 371 of international application no. PCT/EP03/04203 filed Apr. 23, 2003, which is based on German Application No. DE 102 18 147.0, filed Apr. 23, 2002, and claims priority thereto.

BACKGROUND OF THE INVENTION

The present invention relates to water-absorbing polymer particles which respectively delay the decomposition of body fluids or are antimicrobial; processes for producing such polymer particles; the polymer particles obtainable by these processes, fibers, films, foams or foamed masses comprising such polymer particles; composites comprising such polymer particles; as well as the use of such water-absorbing polymer particles, composite, fibers, films, foams or foamed bodies for producing hygiene and medical articles such as diapers, sanitary napkins or incontinence articles and wound dressings for prevention or treatment of skin irritations arising from excretions and body fluids, preferably nappy rash, as well as for treatment of open wounds.

Through the contact of the skin of the wearer with the excretions and body fluids such as urine and excrement of the wearer which arise when wearing hygiene articles, skin irritations, in particular inflammations, for example the so-called nappy rash, can occur at the body parts covered by the hygiene articles. The occurrence of such skin irritations mostly has as a consequence that the hygiene article can not be worn until the healing of the skin irritation. For the wearer, besides the pain occurring with the skin irritation, a significant loss of mobility and independence is also linked to this.

According to the generally prevailing opinion, such skin irritations are predominantly caused by irritants contained in the urine or excrement of the wearer of a hygiene article, in particular by their decomposition. This can be caused or accelerated by microbes.

Furthermore, besides the particular smell of urine and excrement, further unpleasant odors arise over time, which above all can be linked back to the decomposition thereof. Odors of this type are mostly considered as extremely unpleasant by the wearer and his environment.

In the past, numerous attempts were made to make available water-absorbing polymers which have a delaying effect on the decomposition of body fluids or which contribute to the suppression of the formation of unpleasant odors.

U.S. Pat. No. 6,277,772 B1 teaches the loading of superabsorbing polymer powder, with a size within the range of 100 to 800 µm, with a zeolite powder, which has a particle size within a range between 0.5 and 20 µm and has been charged with antimicrobial cations, for example silver ions. The teaching disclosed in this U.S. patent is disadvantageous, since on the one hand the antimicrobial, water-absorbing polymer must be produced in several steps, and on the other hand, it is disadvantageous that in the contact and the charging with zeolites of the above-mentioned particle size, the danger of dust formation is increased, which increase the health risks both for the workers entrusted with the production of an antimicrobial water-absorbing polymer of this type and for the wearers of hygiene articles comprising these antimicrobial water-absorbing polymers.

WO 01/41819 A1 teaches the use of poorly soluble silver salts or colloidal silver in the production of antimicrobial water-absorbent polymers. Thus, according to this disclosure, colloidal silver or the respective insoluble or poorly soluble silver salts can be added to the monomer solution before the polymerization, or the colloidal silver or the respectively insoluble or poorly soluble silver salts can be applied to the already dried water-absorbing polymer particles. Both process variants are disadvantageous. With the addition of colloidal silver or respectively insoluble or poorly soluble silver salts to the monomer solution, because of the respectively poor solubility or insolubility, a relatively inhomogeneous distribution of the silver salts or of the colloidal silver is obtained. The superficial application of respectively poorly soluble or insoluble silver salts or of colloidal silver leads to these adhering relatively badly to the surface of the water-absorbing polymer particles and mostly further auxiliaries, for example zeolites or surfactants, are necessary for fixing the respectively poorly soluble or insoluble silver salts or the colloidal silver to the surface of the water-absorbing polymer particles. Both the inhomogeneous distribution and the poor surface adhesion lead additionally to an increased separation of respectively silver or silver salts and the water-absorbing polymer particle during transport, storage and in particular the conversion which generates a high mechanical load.

Argyria, permanent dark discoloration of skin caused by overuse of medicinal silver preparations, arising through long exposure of the skin to silver is also generally known. The absorption of silver further leads easily to permanent skin coloration. It results therefrom that also here the surface and inhomogeneous distribution with regions of clearly higher concentration of silver salts or colloidal silver is disadvantageous, since this leads to a higher exposure with the skin surface and thereby increases the risk of an argyria.

BRIEF SUMMARY OF THE PRESENT INVENTION

In general, the object of the present invention lies in overcoming the disadvantages arising from the stage of the art.

In particular, an object according to the invention includes in making available water-absorbing antimicrobial polymer particles, which have available sufficient antimicrobial effects, which are maintained over a sufficiently long period of time.

A further object according to the invention includes in achieving a sufficient antimicrobial effect with as small as possible a decrease of the pH value below the normal pH value of the healthy skin surface.

Furthermore, an object according to the invention lies in making available a process with which antimicrobial, water-absorbing polymer articles are produced in as few and as cost-favourable process steps as possible.

In addition, an object according to the invention includes in making available antimicrobial water-absorbing polymer particles, whose ability to decompose body fluids is not substantially influenced by transport, storage or conversion.

According to a further object according to the invention, antimicrobial water-absorbing polymer particles should be made available, which can be incorporated into hygiene articles, which are suitable for respectively prevention or treatment of skin irritations, in particular of nappy rash, preferably with reduced risk of argyria.

Another object according to the invention further includes in creating a process which allows the production of antimicrobial, water-absorbing polymer particles in which the antimicrobial agent is distributed as evenly as possible.

DETAILED DESCRIPTION OF THE PRESENT INVENTION

The above objects are solved by a water-absorbing, antimicrobial polymer particle including from about 1 to about 500 ppm, preferably from about 5 to about 300 ppm, particularly preferably from about 10 to about 70 ppm and even more preferably from about 20 to about 50 ppm, based on the polymer particle, of a silver ion based on a silver salt as ion concentration, wherein the silver salt has a solubility product, preferably a solubility product in water, particularly preferably a solubility product in water at a temperature of about 25° C., of at least about $1 \times 10^{-8}$ $(mol/l)^{m+n}$, preferably of at least about $1 \times 10^{-7}$ $(mol/l)^{m+n}$, particularly preferably of at least about $1 \times 10^{-6}$ $(mol/l)^{m+n}$, even more preferably of at least about $1 \times 10^{-5}$ $(mol/l)^{m+n}$, yet more preferably of at least about $1 \times 10^{-4}$ $(mol/l)^{m+n}$ and most preferably of at least about $1 \times 10^{-3}$ $(mol/l)^{m+n}$; at least about 10 wt.-%, preferably at least about 50 wt.-% and particularly preferably at least about 80 wt.-%, based on polymer particle, of a water-absorbing polymer, based on (α1) from about 50 to about 99.99 wt.-%, preferably from about 70 to about 99.99 wt.-% and particularly preferably from about 85 to about 99.99 wt.-% of polymerized, ethylenically unsaturated, acid groups-containing monomers or salts thereof or mixtures thereof, (α2) 0 to about 40 wt-%, preferably from about 1 to about 30 wt.-% and particularly preferably from about 5 to about 20 wt.-% of polymerized, monoethylenically unsaturated monomers, polymerizable with (α1), (α3) from about 0.01 to about 5 wt.-%, preferably from about 0.1 to about 3 wt.-% and particularly preferably from about 0.5 to about 2 wt.-% of one or more crosslinkers, (α4) 0 to about 30 wt.-%, preferably from about 1 to about 20 wt.-% and particularly preferably from about 5 to about 10 wt.-% of a water-soluble polymer as well as (α5) 0 to about 20 wt.-%, preferably from about 0.01 to about 7 wt-% and particularly preferably from about 0.05 to about 5 wt.-% of one or more auxiliaries, wherein the sum of the weight quantities (α1) to (α5) amounts to about 100 wt. %; optionally, suitable additives; wherein the concentration of the silver ion based on the silver salt in at most about 90 vol.-%, preferably in at most about 70 vol.-%, particularly preferably in at most about 30 vol.-% and even more preferably in no part of the water-absorbing, antimicrobial polymer particle is less than about 0.01 ppm, preferably about 0.5 ppm and particularly preferably about 0.9 ppm and wherein the water-absorbing antimicrobial polymer particle is post-crosslinked with a post-crosslinker in a quantity within a range of from about 0.01 to about 30 wt.-%, preferably from about 0.1 to about 20 wt.-% and particularly preferably from about 0.5 to about 10 wt.-%, respectively based on the weight of the untreated, preferably not yet combined with the post-crosslinker polymer particle.

The above objects are also solved by a water-absorbing, antimicrobial polymer particle, including from about 1 to about 500 ppm, preferably from about 5 to about 300 ppm, particularly preferably from about 10 to about 70 ppm and even more preferably from about 20 to about 50 ppm, based on the polymer particle, of a silver ion based on a silver salt as ion concentration, wherein the silver salt has a solubility product, preferably a solubility product in water, particularly preferably a solubility product in water at a temperature of about 25° C., of at least about $1 \times 10^{-8}$ $(mol/l)^{m+n}$, preferably of at least about $1 \times 10^{-7}$ $(mol/l)^{m+n}$, particularly preferably of at least about $1 \times 10^{-6}$ $(mol/l)^{m+n}$, even more preferably of at least about $1 \times 10^{-5}$ $(mol/l)_{m+n}$, yet more preferably of at least about $1 \times 10^{-4}$ $(mol/l)^{m+n}$ and most preferably of at least about $1 \times 10^{-3}$ $(mol/l)^{m+n}$; at least about 10 wt.-%, preferably at least about 50 wt.-% and particularly preferably at least about 80 wt.-%, based on polymer particle, of a water-absorbing polymer, based on (α1) from about 50 to about 99.99 wt.-%, preferably from about 70 to about 99.99 wt.-% and particularly preferably from about 85 to about 99.99 wt.-% of polymerized, ethylenically unsaturated, acid groups-containing monomers or salts thereof or mixtures thereof, (α2) 0 to about 40 wt-%, preferably from about 1 to about 30 wt.-% and particularly preferably from about 5 to about 20 wt.-% of polymerized, monoethylenically unsaturated monomers, polymerizable with (α1), (α3) 0.01 to about 5 wt.-%, preferably from about 0.1 to about 3 wt.-% and particularly preferably from about 0.5 to about 2 wt.-% of one or more crosslinkers, (α4) 0 to about 30 wt.-%, preferably from about 1 to about 20 wt.-% and particularly preferably from about 5 to about 10 wt.-% of a water-soluble polymer as well as (α5) 0 to about 20 wt.-%, preferably from about 0.01 to about 7 wt-% and particularly preferably from about 0.05 to about 5% wt.-% of one or more auxiliaries, wherein the sum of the weight quantities (α1) to (α5) amounts to about 100 wt. %; optionally, suitable additives; wherein the concentration of the silver ion based on the silver salt in at most about 90 vol.-%, preferably in at most about 70 vol.-%, particularly preferably in at most about 30 vol.-% and even more preferably in no part of the water-absorbing, antimicrobial polymer particle is less than about 0.01 ppm, preferably about 0.5 ppm and particularly preferably about 0.9 ppm and wherein the pH value of the water-absorbing polymer, preferably the pH value of about 1 g of the polymer in about 1 l water according to ERT 400.1-99, lies within a range of from about 4.5 to about 7, preferably of from about 5.2 to about 6.5 and particularly preferably within a range of from about 5.3 to about 6.2.

In a preferred embodiment according to the invention of the water-absorbing, antimicrobial polymer particles according to the invention, the concentration of the silver ion based on a silver salt lies, in no part of the water-absorbing, antimicrobial polymer particles, outside the ion concentration +/−about 30%, preferably +/−about 15% and particularly preferably +/−about 5%, based on the ion concentration.

In a preferred embodiment according to the invention of the water-absorbing, antimicrobial polymer particles, these comprise from about 1 to about 500 ppm, preferably from about 5 to about 300 ppm, particularly preferably from about 10 to about 70 ppm and even more preferably from about 20 to about 50 ppm, based on the polymer particles, a silver ion based on the silver salt, whereby each part of the polymer particles comprises the above-described concentration of the silver ion.

The water-absorbing, antimicrobial polymer particles according to the invention are generally substantially ball-shaped, preferably as obtainable by a grinding process, flake-like or present as pellets. Preferably, the water-absorbing antimicrobial polymer particles according to the invention have a particle size which lies between about 150 and about 850 μm in at least about 20 wt.-%, preferably at least about 50 wt.-% and particularly preferably at least about 80 wt.-%. The particle size is determined in that the particles fall through a sieve with a mesh size of about 850 μm and remain on a sieve with a mesh size of about 150 μm.

The monoethylenically unsaturated, acid group-containing monomers (α1) can be partially or fully, preferably partially neutralized. Preferably the monoethylenically unsaturated, acid group-containing monomers are neutralized to at least about 25 mol. %, particularly preferably to at least about 40 mol % and even more preferably to from about 40 to about 90 mol. %. The neutralization of the monomers (α1) can occur before and also after the polymerization. Further, the neutralization can occur with alkali metal hydroxides, alkaline earth metal hydroxides, ammonia as well as carbonates and bicarbonates. In addition, every further base is conceivable which forms a water-soluble salt with the acid. A mixed neutralization with different bases is also conceivable. Neutralization with ammonia or with alkali metal hydroxides is preferred, particularly preferred with sodium hydroxide or with ammonia.

Preferred monoethylenically unsaturated, acidic group-containing monomers (α1) are acrylic acid, methacrylic acid, ethacrylic acid, α-chloroacrylic acid, α-cyanoacrylic acid, β-methylacrylic acid (crotonic acid), α-phenylacrylic acid, β-acryloxypropionic acid, sorbinic acid, α-chlorosorbinic acid, 2'-methylisocrotonic acid, cinnamic acid, p-chlorocinnamic acid, β-stearic acid, itaconic acid, citraconic acid, mesaconic acid, glutaconic acid, aconitic acid, maleic acid, fumaric acid, tricarboxythylene and maleic acid anhydride, wherein acrylic acid and methacrylic acid are particularly and acrylic acid even more particularly preferred.

Besides these carboxylate group-containing monomers, further preferred mono-ethylenically unsaturated acidic group-containing monomers (α1) are ethylenically unsaturated sulfonic acid monomers or ethylenically unsaturated phosphonic acid monomers.

Preferred ethylenically unsaturated sulfonic acid monomers are allylsulfonic acid or aliphatic or aromatic vinylsulfonic acids or acrylic or methacrylic acids. Preferred aliphatic or aromatic vinylsulfonic acids are vinylsulfonic acid, 4-vinylbenzylsulfonic acid, vinyltoluenesulfonic acid and styrenesulfonic acid. Preferred acrylic or methacrylic acids are sulfoethyl(meth)acrylate, sulfopropyl(meth)acrylate and 2-hydroxy-3-methacryloxypropylsulfonic acid. As (meth) acrylamidoalkylsulfonic acid, 2-acrylamido-2-methylpropanesulfonic acid is preferred.

As ethylenically unsaturated phosphonic acid monomers are preferred vinylphosphonic acid, allylphosphonic acid, vinylbenzylphosphonic acid, (meth)acrylamidoalkylphosphonic acids, acrylamidoalkyldiphosphonic acids, phosphonomethylated vinylamines and (meth)acrylphosphonic acid derivatives.

It is preferred according to the invention that the water-absorbing polymer comprises at least about 50 wt. %, preferably at least about 70 wt. % and more preferably at least about 90 wt. % carboxylate group-containing monomers. It is particularly preferred according to the invention that the water-absorbing polymer comprises at least about 50 wt. %, preferably at least about 70 wt. % acrylic acid, which is neutralized preferably to at least about 20 mol %, particularly preferably to at least about 40 mol %.

Preferred ethylenically unsaturated monomers containing a protonated nitrogen, which can be present besides the monoethylenically unsaturated, acid groups-containing monomers (α1), are preferably dialkylaminoethyl(meth) acrylates in the protonated form, for example dimethylaminoethyl(meth)acrylate hydrochloride or dimethylaminoethyl (meth)acrylate hydrosulfate, as well as dialkylaminoalkyl (meth)acrylamides in the protonated form, for example dimethylaminoethyl(meth)acrylamide hydrochloride, dimethylaminopropyl(meth)acrylamide hydrochloride, dimethylaminopropyl(meth)acrylamide hydrosulfate or dimethylaminoethyl(meth)acrylamide hydrosulfate.

Preferred ethylenically unsaturated monomers containing a quaternated nitrogen, which can be present besides the monoethylenically unsaturated, acid groups-containing monomers (α1), are dialkylammoniumalkyl(meth)acrylates in quaternated form, for example trimethylammoniumethyl (meth)acrylate-methosulfate or dimethylethylammoniumethyl(meth)acrylate-ethosulfate as well as (meth)acrylamidoalkyldialkylamine in quatemated form, for example (meth) acrylamidopropyltrimethylammonium chloride, trimethylammoniumethyl(meth)acrylate chloride or (meth) acrylamidopropyltrimethylammonium sulfate.

As monoethylenically unsaturated monomers (α2) which can be co-polymerized with (α1) are preferred acrylamides and (meth)acrylamides.

Possible (meth)acrylamides besides acrylamide and methacrylamide are alkyl-substituted (meth)acrylamides or aminoalkyl-substituted derivatives of (meth)acrylamide such as N-methylol(meth)acrylamide, N,N-dimethylamino(meth) acrylamide, dimethyl(meth)acrylamide or diethyl(meth) acrylamide. Possible vinylamides are for example N-vinylamides, N-vinylformamides, N-vinylacetamides, N-vinyl-N-methylacetamides, N-vinyl-N-methylformamides, vinylpyrrolidone. Among these monomers acrylamide is particularly preferred.

Additionally preferred monoethylenically unsaturated monomers (α2) which are copolymerizable with (α1) are water-dispersible monomers. Preferred water-dispersible monomers are acrylic acid esters and methacrylic acid esters, such as methyl(meth)acrylate, ethyl(meth)acrylate, propyl(meth)acrylate or butyl(meth)acrylate, as well as vinylacetate, styrene and isobutylene.

Preferred cross-linkers (α3) according to the invention are compounds which have at least two ethylenically unsaturated groups in one molecule (cross-linker class I), compounds which have at least two functional groups which can react with functional groups of the monomers (α1) or (α2) in a condensation reaction (=condensation cross-linkers), in an addition reaction or a ring-opening reaction (cross-linker class II), compounds which have at least one ethylenically unsaturated group and at least one functional group which can react with functional groups of the monomers (α1) or (α2) in a condensation reaction, an addition reaction or a ring-opening reaction (cross-linker class III), or polyvalent metal cations (cross-linker class IV). Thus with the compounds of cross-linker class I a cross-linking of the polymer is achieved by radical polymerization of the ethylenically unsaturated groups of the cross-linker molecules with the mono-ethylenically unsaturated monomers (α1) or (α2), while with the compounds of cross-linker class II and the polyvalent metal cations of cross-linker class IV a cross-linking of the polymer is achieved respectively via condensation reaction of the functional groups (cross-linker class II) or via electrostatic interaction of the polyvalent metal cation (cross-linker class IV) with the functional groups of the monomer (α1) or (α2). With compounds of cross-linker class III a cross-linking of the polymers is achieved correspondingly by radical polymerization of the ethylenically unsaturated groups or also by condensation reaction between the functional groups of the cross-linkers and the functional groups of the monomers (α1) or (α2).

Preferred compounds of cross-linker class I are poly(meth) acrylic acid esters, which have been obtained for example by conversion of a polyol, such as for example ethylene glycol, propylene glycol, trimethylolpropane, 1,6-hexanediol, glycerine, pentaerythritol, polyethyleneglycol or polypropyleneglycol, of an aminoalcohol, a polyalkylenepolyamine, such as for example diethylenetriamine or triethylenetetraamine, or of an alkoxidised polyol with acrylic acid or methacrylic acid. Further preferred compounds of cross-linker class I are polyvinyl compounds, poly(meth)allyl compounds, (meth) acrylic acid esters of a monovinyl compound or (meth)acrylic acid esters of a mono(meth)allyl compound, preferably of the mono(meth)allyl compounds of a polyol or of an aminoalcohol. In this context DE 195 43 366 and DE 195 43 368 are referred to.

Preferred crosslinkers of crosslinker classes II, III and IV are those crosslinkers which are disclosed in WO 01/41819 and those which fullfill the above described properties of the crosslinkers of crosslinker classes II, III and IV.

As water-soluble polymers ($\alpha 4$), water-soluble polymers such as those comprising partially or fully saponified polyvinyl alcohol, polyvinylpyrrolidone, starches or starch derivatives, polyglycols or polyacrylic acids can preferably be polymerized into the water-absorbing polymer according to the invention. The molecular weight of these polymers is not critical, as long as they are water soluble. Preferred water soluble polymers are starches or starch derivatives or polyvinyl alcohol. The water soluble polymers, preferably synthetic like polyvinyl alcohol, can also serve as graft basis for the monomers to be polymerized.

As auxiliary ($\alpha 5$), suspension agents, odor binders, surface-active agents, or anti-oxidants are preferably used.

As additives, materials are particularly suitable which contribute to the stabilization of the silver ion or of the silver salt. Of particular interest here are materials which can prevent or at least delay the coloration caused by silver of the water-absorbing, antimicrobial polymer according to the invention.

In addition, further compounds can be incorporated into the water-absorbing, antimicrobial polymer particles according to the invention, in particular to prevent the washing-out of silver ions or of elemental silver forming. Among these, surfactants are preferred, as, for example, described in WO 01/41819.

According to a preferred embodiment, the water-absorbing, antimicrobial polymer particles according to the invention are present as substantially ball-shaped or pellet-like particles, which have a concentration of a silver ion based on a silver salt within the range of from about 1 to about 500 ppm, preferably within the range of from about 5 to about 300 ppm and particularly preferably within the range of from about 10 to about 70 ppm.

It is further preferred according to the invention that the water-absorbing, antimicrobial polymer particles comprise an inner part, an outer part surrounding the inner part as well as a surface part surrounding the outer part, wherein the outer part has a higher degree of crosslinking than the inner part, so that preferably a core-shell structure forms. The increased crosslinking in the surface part of the polymer particles is preferably achieved by post-crosslinking of reactive groups in proximity to the surface. This post-crosslinking can occur thermally, photochemically or chemically. More precise details regarding the post-crosslinking conditions can be taken from the following details concerning the process according to the invention for producing water-absorbing, antimicrobial polymer particles.

The invention further relates to a process for producing a water-absorbing antimicrobial polymer particle, whereby as reagents ($\beta 1$) from about 50 to about 99.99 wt.-%, preferably from about 70 to about 99.99 wt.-%, particularly preferably from about 85 to about 99.99 wt.-% of polymerized, ethylenically unsaturated, acid groups-containing polymers or salts thereof or mixtures thereof, ($\beta 2$) 0 to about 40 wt.-%, preferably from about 1 to about 30 wt.-% and particularly 20 preferably from about 5 to about 20 wt.-% of polymerized, monoethylenically unsaturated monomers polymerizable with ($\beta 1$), ($\beta 3$) from about 0.01 to about 5 wt.-%, preferably from about 0.1 to about 3 wt.-% and particularly preferably from about 0.5 to about 2 wt.-% of one or more crosslinkers, ($\beta 4$) 0 to about 30 wt.-%, preferably from about 1 to about 20 wt.-% and particularly preferably from about 5 to about 10 wt.-% of a water-soluble polymer as well as ($\beta 5$) 0 to about 20 wt.-%, preferably from about 0.01 to about 7 wt.-% and particularly preferably from about 0.05 to about 5 wt.-% of one or more auxiliaries, wherein the sum of the weight quantities ($\beta 1$) to ($\beta 5$) amounts to about 100 wt %, are polymerized together with formation of a water-absorbing polymer; wherein from about 1 to about 500 ppm, preferably from about 5 to about 300 ppm of a silver ion in the form of a water soluble silver salt, which has a solubility product, preferably a solubility product in water, particularly preferably a solubility product in water at a temperature of about 25° C., of at least about $1 \times 10^{-8}$ $(mol/l)^{m+n}$, preferably of at least about $1 \times 10^{-7}$ $(mol/l)^{m+n}$, particularly preferably of at least about $1 \times 10^{-6}$ $(mol/l)^{m+n}$, even more preferably of at least about $1 \times 10^{-5}$ $(mol/l)^{m+n}$, yet more preferably of at least about $1 \times 10^{-4}$ $(mol/l)^{m+n}$, and most preferably of at least about $1 \times 10^{-3}$ $(mol/l)_{m+n}$, dissolved in a solvent, based on the reagents, is added to the reagents before the end of the formation of the water-absorbing polymer, and wherein the water-absorbing polymer is comminuted, dried and optionally ground and is post-crosslinked in a post-crosslinking step with a post-crosslinker in a quantity within a range of from about 0.01 to about 30 wt. %, based on the as yet untreated polymer particle, preferably of the polymer particle not yet combined with the post-crosslinker.

The invention further relates to a process for producing a water-absorbing antimicrobial polymer particle, whereby as reagents ($\beta 1$) from about 50 to about 99.99 wt.-%, preferably from about 70 to about 99.99 wt.-%, particularly preferably from about 85 to about 99.99 wt.-% of polymerized, ethylenically unsaturated, acid groups-containing polymers or salts thereof or mixtures thereof, ($\beta 2$) 0 to about 40 wt.-%, preferably from about 1 to about 30 wt.-% and particularly preferably from about 5 to about 20 wt.-% of polymerized, monoethylenically unsaturated monomers polymerizable with ($\beta 1$), ($\beta 3$) from about 0.01 to about 5 wt.-%, preferably from about 0.1 to about 3 wt.-% and particularly preferably from about 0.5 to about 2 wt.-% of one or more crosslinkers, ($\beta 4$) 0 to about 30 wt.-%, preferably from about 1 to about 20 wt.-% and particularly preferably from about 5 to about 10 wt.-% of a water-soluble polymer as well as ($\beta 5$) 0 to about 20 wt.-%, preferably from about 0.01 to about 7 wt.-% and particularly preferably from about 0.05 to about 5 wt.-% of one or more auxiliaries, wherein the sum of the weight quantities ($\beta 1$) to ($\beta 5$) amounts to about 100 wt. %, are polymerized together with formation of a water-absorbing polymer; wherein from about 1 to about 500 ppm, preferably from about 5 to about 300 ppm of a silver ion in the form of a water soluble silver salt, which has a solubility product, preferably a solubility product in water, particularly preferably a solubility product in water at a temperature of about 25° C., of at least about $1 \times 10^{-8}$ $(mol/l)^{m+n}$, preferably of at least about $1 \times 10^{-7}$ $(mol/l)^{m+n}$, particularly preferably of at least about $1 \times 10^{-6}$ $(mol/l)^{m+n}$, even more preferably of at least about $1 \times 10^{-5}$ $(mol/l)^{m+n}$, yet more preferably of at least about $1 \times 10^{-4}$ $(mol/l)^{m+n}$ and most preferably of at least about $1 \times 10^{-3}$ $(mol/l)^{m+n}$, dissolved in a solvent, based on the reagents, is added to the reagents before the end of the formation of the water-absorbing polymer, and wherein the ethylenically unsaturated, acid groups-containing monomers ($\beta 1$) are neutralized such that the pH value of the water-absorbing, anti microbial polymer particles lies within the range of from about 4.5 to about 7.

According to a preferred embodiment of the process according to the invention, the silver salt is dissolved in the same solvent as that in which the monomers are dissolved. According to a variant of the process according to the invention, it is preferred that the silver salt is added beforehand to the solvent in which the monomer is then taken up. In general, the quantity of the silver salt which is combined with the solvent is selected so that the concentration of the silver ion based on the silver salt in the prepared water-absorbing antimicrobial polymer particle amounts to from about 1 to about 500 ppm. Preferably, the concentration of the silver salt lies within the range of from about 0.003 to about 0.5 grams per liter solvent, preferably within the range of from about 0.003 to about 0.1 g/l solvent, and particularly preferably within the range of from about 0.005 to about 0.05 g/l solvent, which is then used for dissolving the monomers. In another variant of the process according to the invention, the silver salt is dissolved in a solvent and the thus formed silver salt solution added to the monomer solution. In this case also, the concentration ratios are selected in dependence on the quantity of solvent which is used for taking up the monomer in such a way that in the prepared water-absorbing anti microbial polymer particles, the concentration of the silver ion based on a silver salt lies within the range of from about 1 to about 500 ppm.

As solvent, all solvents which are suitable to the skilled person can be used, in which the silver salts used in the process according to the invention are slightly soluble. As solvent are considered in particular water and lower alcohols, in particular methanol, ethanol, propanol, isopropanol and butanol, wherein it is preferred according to the invention that the solvent is based on water to at least about 50 wt. %, preferably at least about 70 wt. % and particularly preferably at least about 90 wt. %, based on the solvent.

The polymerization of the processes according to the invention is then considered as finished, when the residual monomer content lies below about 1%, based on the used monomers. In the process according to the invention, the silver salt dissolved in a solvent can be added to the reagents preferably up to a residual monomer content of about 10 wt. %, particularly preferably up to a residual monomer content of about 50 wt. % and even more preferably up to a residual monomer content of about 80 wt. % as well as yet more preferably before the start of the polymerization reaction, i.e. at a residual monomer content of about 100 wt. %, respectively based on the monomers used.

Through the process conducted according to the invention, as homogeneous as possible a distribution of the silver ion based on a silver salt is achieved.

In respect of the reagents ($\beta 1$) to ($\beta 5$), reference is made to the details concerning ($\alpha 1$) to ($\alpha 5$).

The water-absorbing polymer can be produced from the above-named monomers and cross-linkers by various polymerization means. For example, in this context can be named bulk polymerization which occurs preferably in kneading reactors such as extruders or by band polymerization, solution polymerization, spray polymerization, inverse emulsion polymerization and inverse suspension polymerization. Solution polymerization is preferably carried out in water as solvent. The solution polymerization can occur continuously or discontinuously, as can the other above-mentioned polymerization types. The solution polymerization preferably occurs as continuously running band polymerization. From the prior art a broad spectrum of variation possibilities can be learnt with respect to reaction proportions such as temperatures, type and quantity of the initiators as well as of the reaction solution. Typical processes are described in the following patent specifications: U.S. Pat. No. 4,286,082, DE 27 06 135, U.S. Pat. No. 4,076,663, DE 35 03 458, DE 40 20 780, DE 42 44 548, DE 43 23 001, DE 43 33 056, DE 44 18 818.

Particularly preferably, the processes according to the invention can be used in the belt polymerization of the water-absorbing antimicrobial polymer. Generally, the Mulden belt used in these processes comprises only little or no stirring means such as stirrers or kneading hooks. In this way, by the use of the process according to the invention a good distribution of the silver ion based on a silver salt can be achieved without separate stirring means.

Another possibility for producing the water-absorbing polymers is to first produce non-crosslinked, in particular linear pre-polymers, preferably by radical means from the above-mentioned monoethylenically unsaturated monomers ($\alpha 1$) or ($\alpha 2$) (or respectively ($\beta 1$) and ($\beta 2$)) and then to convert these with reagents acting as a crosslinker ($\alpha 3$) (or respectively ($\beta 3$)), preferably with those of classes II and IV. This variant is preferably then used if the water-absorbing polymer should be first processed in form-giving processes, for example into fibers, films or other flat structures such as fabrics, woven fabrics, webs or non-woven materials, and cross-linked in this form.

It is further preferred in the processes according to the invention, to comminute, dry and optionally to grind the water-absorbing polymer and to convert the thus further processed water-absorbing polymer in a so-called "post-crosslinking step" with further crosslinkers, so-called "post-crosslinkers" and optionally to treat it thermally again.

Preferred as post-crosslinker are the compounds of crosslinker classes II and IV cited in the context of the crosslinkers.

Among these compounds, particularly preferred as post-crosslinker are diethylene glycol, triethylene glycol, polyethylene glycol, glycerol, polyglycerol, propylene glycol, diethanolamine, triethanolamine, polyoxypropylene, oxyethylene/oxypropylene block copolymers, sorbitan fatty acid esters, polyoxyethylenesorbitan fatty acid esters, trimethylolpropane, pentaerythritol, polyvinyl alcohol, sorbitol, 1,3-dioxolan-2-one (ethylene carbonate), 4-methyl-1,3-dioxolan-2-one (propylene carbonate), 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dimethyl-1,3-dioxan-2-one, 1,3-dioxolan-2-one, poly-1,3-dioxolan-2-one.

Particularly preferably, ethylene carbonate is used as post-crosslinker.

These compounds are preferably used in an amount in the range from about 0.01 to about 30, preferably from about 0.1 to about 20 and particularly preferably from about 0.5 to about 10 wt. %, based on the as yet untreated polymer, preferably on the polymer not yet combined with the post-crosslinker. Organic solvents may be added to the mixture in an amount of 0 to about 60, preferably from about 0.1 to about 40 and particularly preferably from about 0.2 to about 50 wt. %, based on the as yet untreated polymer. As organic solvents there are preferably used lower alcohols such as methanol, ethanol, n-propanol, isopropanol, n-butanol, isobutanol, sec.-butanol and tert.-butanol, ketones such as acetone, methyl ethyl ketone and methyl isobutyl ketone, ethers such as dioxane, tetrahydrofuran and diethyl ether, amides such as N,N-dimethylformamide and N,N-diethylformamide, as well as sulfoxides such as dimethyl sulfoxide.

It is further preferred for the water-absorbing antimicrobial polymer particles according to the invention and the processes in one embodiment, that from about 30 to about 80 mol %, preferably from about 40 to about 70 mol % and particularly preferably from about 50 to about 65 mol % of the acid groups from the ethylenically unsaturated, acid groups-containing monomers of the water-absorbing polymer are neutralized with an alkali or alkaline earth salt, preferably an alkali salt and particularly preferably sodium hydroxide. The neutralisation preferably occurs according to the invention in such a way that the pH value of the water-absorbing antimicrobial polymer particle according to the invention lies within the range of from about 4.5 to about 7, preferably of from about 5.2 to about 6.5 and particularly preferably of from about 5.3 to about 6.2. By means of a neutralisation of this type, on the one hand the skin tolerance to the water-absorbing antimicrobial polymer particle according to the invention is increased and additionally the odor binding ability of the water-absorbing polymer particle according to the invention is improved.

In addition, it is preferred for the water-absorbing, antimicrobial polymer particles according to the invention and the process according to the invention that the silver salt $Ag_mX_n$ has a solubility product, preferably in water, of about $1\times10^{-8}$ $(mol/l)^{m+n}$, preferably of at least about $1\times10^{-7}$ $(mol/l)^{m+n}$, particularly preferably of at least about $1\times10^{-6}$ $(mol/l)_{m+n}$, even more preferably of at least about $1\times10^{-5}$ $(mol/l)_{m+n}$, yet more preferably of at least about $1\times10^{-4}$ $(mol/l)^{m+n}$ and most preferably of at least about $1\times10^{-3}$ $(mol/l)^{m+n}$. In a particular embodiment of the respective processes according to the invention or of the water-absorbing, antimicrobial polymer particles according to the invention, a silver salt is respectively used or a silver salt is comprised, of which, at a temperature of about 25° C., at least about Ig, preferably at least about 5 g, particularly preferably at least about 10 g, even more preferably at least about 50 g, yet more preferably at least about 100 g and most preferably at least about 200 g can be fully dissolved in about 100 g water.

It is further preferred that in the water-absorbing, antimicrobial polymer particles according to the invention and in the process according to the invention the silver salt is silver nitrate. Besides silver nitrate, other inorganic or organic silver salts can be used. In this context are cited as examples of inorganic silver salts, silver carbonate, silver sulphate, silver hydrogensulphate, silver alum or silver phosphate. As organic silver salts are considered silver acrylate, silver citrate, silver lactate, silver acetate, silver toluene-sulfonate, silver benzoate, silver trifluoromethanesulfonate or, in the case of silver acrylate, polymers thereof. Each of the above-mentioned silver salts can be respectively comprised in the antimicrobial, water-absorbing polymer particles according to the invention or used in the process according to the invention and thereby represent a preferred embodiment respectively of the water-absorbing, antimicrobial polymer particles according to the invention or of the process according to the invention. Silver nitrate-comprising antimicrobial, water-absorbing polymer particles according to the invention are, of these, most preferred.

In addition, the invention relates to water-absorbing, antimicrobial polymer particles which are obtainable by the above processes. Preferably, the water-absorbing, antimicrobial polymer particles obtainable by the above processes have the same properties as the previously described water-absorbing, antimicrobial polymer particles according to the invention.

Preferably, the water-absorbing, antimicrobial polymer particles according to the invention have at least one, preferably each, of the following properties:

(A) the maximum absorption of a about 0.9 wt. % aqueous NaCl solution according to ERT 440.1-99 is in a range from at least about 10 to about 1000 g/g, preferably from about 15 to about 500 and particularly preferably from about 20 to about 300 g/g, (B) the part that can be extracted with a about 0.9 wt. % aqueous NaCl solution according to ERT 470.1-99 is less than about 30 wt. %, preferably less than about 20 wt. % and particularly preferably less than about 10 wt. %, respectively based on the polymer, (C) the bulk density according to ERT 460.1-99 is in the range from about 300 to about 1000 g/l, preferably from about 310 to about 800 g/l and particularly preferably from about 320 to about 700 g/l, (D) the pH value according to ERT 400.1-99 of Ig of the untreated absorbing polymer structure in about 1 liter of water is in the range from about 4 to about 10, preferably from about 4 to about 7, particularly preferably from about 5.2 to about 6.5, and even more preferably from about 5.3 to about 6.2;

(E) the Centrifuge Retention Capacity (CRC) according to ERT 441.1-99 is in the range from about 10 to about 100 g/g, preferably from about 15 to about 80 g/g, and particularly preferably from about 20 to about 60 g/g.

The property combinations of two or more properties of the properties listed above represent respectively preferred embodiments of the process according to the invention. Further particularly preferred embodiments according to the invention are water-absorbing antimicrobial polymer particles which exhibit the following properties or property combinations identified by letters or combinations of letter: A, B, C, D, E, AB, ABC, ABCD, ABCDE, BC, BCD, BCDE, CD, CDE, DE.

According to a preferred embodiment, the water-absorbing, antimicrobial polymer particles according to the invention have an antimicrobial effect, in which the quantity of $NH_3/h$ after at least about 6, preferably at least about 12 and particularly preferably at least about 24 days does not exceed about 200 ppm, which is derived according to the following processes given under test methods and examples.

The invention also relates to a composite comprising water-absorbing, antimicrobial polymer particles according to the invention, as well as a substrate. It is preferred that the water-absorbing, antimicrobial polymer particles according to the invention and the substrate are firmly combined with one another. Preferred substrates include films formed from polymers, for example from polyethylene, polypropylene or polyamide, metals, non-wovens, fluff, tissues, woven fabrics, natural or synthetic fibers, or other foams.

If the composite is an absorbent core, the water-absorbing, antimicrobial polymer particle according to the invention is incorporated into a substrate. This substrate is preferably fibrous materials. Fibrous materials which can be used in the present invention comprise natural fibers (modified or unmodified) as well as synthetic fibers. Examples of suitable unmodified and modified natural fibers comprise cotton, Esparto grass, sugar-cane, kemp, flax, silk, wool, cellulose, chemically modified cellulose, jute, rayon, ethyl-cellulose and cellulose acetate. Suitable synthetic fibers can be produced from polyvinyl-chloride, polyvinylfluoride, polytetrafluoroethylene, polyvinylidenechloride, polyacrylates such as Orion®, Polyvinylacetate, polyethylvinylacetate, soluble or insoluble polyvinylalcohol, polyolefins such as polyethylene (for example PULPEX®) and polypropylenes, polyamides such as nylon, polyesters such as DACRON® or Kodel®, polyurethanes, polystyrenes and the like. The fibers used can comprise only natural fibers, only synthetic fibers or any compatible combination of natural and synthetic fibers. The water-soluble antimicrobial polymer particles are held in the substrate by means of the structure of the substrate or by means of an adhesive or by means of both.

The fibers used in the above invention can be hydrophilic or hydrophobic, or they can comprise a combination of hydrophilic and hydrophobic fibers. The term "hydrophilic" as used here describes fibers or surfaces of fibers which can be wetted by aqueous liquids (for example aqueous bodily liquids) which are deposited on these fibers. Hydrophilicity and wettability are typically defined in terms of the contact angle and the surface tension of the concerned liquids and solids. This is discussed in detail in a publication of the American Chemical Society with the title "Contact Angle, Wettability and Adhesion", published by Robert F. Gould (copyright 1964). A fiber or the surface of a fiber is wetted by a liquid (i.e. it is hydrophilic) if either the contact angle between the liquid and the fiber or the surface thereof amounts to less than 90°, or if the liquid tends to distribute itself spontaneously over the surface, wherein both conditions are normally simultaneous. On the other hand a fiber or the surface of a fiber is considered as hydrophobic, if the contact angle is larger than about 90° and the liquid does not spread spontaneously on the surface of the fiber.

In a particularly preferred embodiment according to the invention, the composite is a diaper. In this case, the components of the diaper that are different from the water-absorbing antimicrobial polymer represent the substrate of the composite. In a preferred embodiment the diaper contains a core described hereinbefore. In this case the constituents of the diaper different from the core constitute the substrate of the composite. In general a composite used as a diaper includes a water-impermeable lower layer, a water-permeable, preferably hydrophobic upper layer, and a layer comprising the absorbing, foam-like polymer structure according to the invention and which is arranged between the lower layer and the upper layer. This layer containing the absorbing foam-like polymer structure according to the invention is preferably a core described hereinbefore. The lower layer may comprise all materials known to the person skilled in the art, whereby polyethylene or polypropylene are preferred. The upper layer may likewise contain all suitable materials known to the person skilled in the art, whereby polyesters, polyolefins, viscose and the like are preferred, which ensure a sufficient liquid permeability of the upper layer. In this context reference is made to the disclosures in U.S. Pat. No. 5,061,295, U.S. Pat. No. Re.26,151, U.S. Pat. No. 3,592,194, U.S. Pat. No. 3,489,148 as well as U.S. Pat. No. 3,860,003.

The invention further relates to the use of a water-absorbing, antimicrobial polymer particle according to the invention in fibers, films, foams, formed bodies or composites. It is here preferred that the water-absorbing antimicrobial polymer particles according to the invention are incorporated into fibers, films, foams, formed bodies.

In addition, the invention relates to the use of a polymer particle according to the invention; or of fibers, films, foams or formed bodies according to the invention; or of composites according to the invention; or at least two therefrom, for production of a hygiene article, in particular of a wound dressing, diaper, sanitary napkin or an incontinence article, for prevention or treatment of skin irritations arising through body excretions, preferably nappy rash or argyria; or for treatment of wounds.

The following examples should more closely describe the invention in a non-limiting way.

Test Methods:

Determination of $NH_3$ Formation

A test bacillus such as bacillus pasteurii is activated overnight at 30° C. in 100 ml liquid culture in the shaking water bath, centrifuged for ten minutes at room temperature and resuspended in synthetic urine (Jayco urine test solution: $Na_2SO_4$ pa 2.00 g, KCl pa 2.00 g $NH_4H_2PO_4$ pa 0.85 g, $(NH_4)_2HPO_4$ pa 0.15 g, $MgCl_2.6H_2O$ pa 0.50 g, $CaCl_2.2H_2O$ 0.25 g, dist. water 994.25 g) respectively 33 ml of the artificial urine combined with bacteria are transferred into conical flasks and combined with 0.5 g superabsorber. The vessels are sealed with a rubber stopper with a hole through which a Drager diffusion capillary is led and incubated at 30° C. in an incubator.

The ammonia liberated is measured in ppm×h. As control, an experiment was carried out simultaneously without SAP. All experiments were carried out as double determinations. The results given represent the mean values.

EXAMPLES

Example 1

(Degree of Neutralization: 70; 0.03 g Silver Nitrate)

0.45 g polyethylene glycol-300-diacrylate and 1.05 g polyethylene glycol-750-monoallylether acrylate as crosslinker are dissolved in 955.985 g of an aqueous solution of sodium acrylate with a degree of neutralization of 70 mol. % (monomer concentration: 37.7%). 0.03 g silver nitrate were dissolved in 10 g water and added to the monomer solution. Nitrogen was then flushed through the monomer solution in a plastic polymerization vessel for 30 minutes in order to remove the dissolved oxygen. At a temperature of 4° C., the polymerization was started by consecutive addition of 0.3 g sodium peroxidisulfate in 10 g dist. water, 0.1 g 2,2'-azobis-2-amidinopropane dihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder ("Fleischwolf") and dried for 2 h at 150° C. in a circulating air oven. The dried product is coarsely ground, ground and the particles of size 150 to 850 µm sieved out for further conversion (powder A).

50 g powder A are mixed with vigorous stirring with a solution of 0.5 g ethylene carbonate and 1.5 g water and then heated for 60 minutes in an oven regulated at 170° C.

Example 2

(Degree of Neutralization: 70; 0.012 g Silver Nitrate)

0.45 g polyethylene glycol-300-diacrylate and 1.05 g polyethylene glycol-750-monoallyletheracrylate as crosslinker are dissolved in 955.997 g of an aqueous solution of sodium acrylate with a degree of neutralization of 70 mol % (monomer concentration 37.7%). 0.012 g silver nitrate are dissolved in 10 g water and added to the monomer solution. Nitrogen is then flushed through the monomer solution in a plastic polymerization vessel for 30 minutes, in order to remove dissolved oxygen. At a temperature of 4° C., the polymerization is started by consecutive addition of 0.3 g sodium peroxidisulfate in 10 g dist. water, 0.1 g 2,2'-azobis-2-amidinopropanedihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder and dried for 2 h at 150° C. in a circulating air oven. The dried product is coarsely ground, ground and the particles of size 150 to 850 μm sieved out for further conversion (powder B).

50 g powder B was mixed with vigorous stirring with a solution of 0.5 g ethylene carbonate and 1.5 g water and then heated for 60 minutes in an oven regulated to 170° C.

Comparative Example 1

(Degree of Neutralization: 70; 0.014 g Freshly Precipitated Silver Chloride)

0.45 g polyethylene glycol-300-diacrylate and 1.05 g polyethylene glycol-750-monoallyletheracrylate as crosslinker are dissolved in 955.985 g of an aqueous solution of sodium acrylate with a degree of neutralization of 70 mol. % (monomer concentration 37.7%). 0.014 g freshly precipitated silver chloride are suspended in 10 g water and added to the monomer solution. Nitrogen is then flushed through the monomer solution in a plastic polymerization vessel for 30 minutes, in order to remove dissolved oxygen. At a temperature of 4° C., the polymerization is started by consecutive addition of 0.3 g sodium peroxidisulfate in 10 g dist. water, 0.1 g 2,2'-azobis-2-amidinopropanedihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder and dried for 2 h at 150° C. in a circulating air oven. The dried product is coarsely ground, ground and the particles of size 150 to 850 μm sieved out for further conversion (powder C).

50 g powder C was mixed with vigorous stirring with a solution of 0.5 g ethylene carbonate and 1.5 g water and then heated for 60 minutes in an oven regulated to 170° C.

Comparative Example 2

(Degree of Neutralization: 70; No Silver)

0.45 g polyethylene glycol-300-diacrylate and 1.05 g polyethylene glycol-750-monoallyletheracrylate as crosslinker are dissolved in 965.988 g of an aqueous solution of sodium acrylate with a degree of neutralization of 70 mol. % (monomer concentration 37.7%). Nitrogen is then flushed through the monomer solution in a plastic polymerization vessel for 30 minutes, in order to remove dissolved oxygen. At a temperature of 4° C., the polymerization is started by consecutive addition of 0.3 g sodium peroxidisulfate in 10 g dist. water, 0.1 g 2,2'-azobis-2-amidinopropanedihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder and dried for 2 h at 150° C. in a circulating air oven. The dried product is coarsely ground, ground and the particles of size 150 to 850 μm sieved out for further conversion (powder D).

50 g powder D was mixed with vigorous stirring with a solution of 0.5 g ethylene carbonate and 1.5 g water and then heated for 60 minutes in an oven regulated to 170° C.

Example 3

(Degree of Neutralization: 50; 0.012 g Silver Nitrate)

0.45 g polyethylene glycol-300-diacrylate and 1.05 g polyethylene glycol-750-monoallyletheracrylate as crosslinker are dissolved in 955.997 g of an aqueous solution of sodium acrylate with a degree of neutralization of 50 mol. % (monomer concentration 37.7%). 0.012 g silver nitrate are dissolved in 10 g water and added to the monomer solution. Nitrogen is then flushed through the monomer solution in a plastic polymerization vessel for 30 minutes, in order to remove dissolved oxygen. At a temperature of 4° C., the polymerization is started by consecutive addition of 0.3 g sodium peroxidisulfate in 10 g dist. water, 0.1 g 2,2'-azobis-2-amidinopropanedihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder and dried for 2 h at 150° C. in a circulating air oven. The dried product is coarsely ground, ground and the particles of size 150 to 850 μm sieved out for further conversion (powder E).

50 g powder E was mixed with vigorous stirring with a solution of 0.5 g ethylene carbonate and 1.5 g water and then heated for 40 minutes in an oven regulated to 160° C.

Comparative Example 3

0.45 g polyethylene glycol-300-diacrylate and 1.05 g polyethylene glycol-750-monoallyletheracrylate as crosslinker are dissolved in 965.988 g of an aqueous solution of sodium acrylate with a degree of neutralization of 50 mol. % (monomer concentration 37.7%). Nitrogen is then flushed through the monomer solution in a plastic polymerization vessel for 30 minutes, in order to remove dissolved oxygen. At a temperature of 4° C., the polymerization is started by consecutive addition of 0.3 g sodium peroxidisulfate in 10 g dist. water, 0.1 g 2,2'-azobis-2-amidinopropanedihydrochloride in 10 g dist. water, 0.07 g 35% hydrogen peroxide solution in 10 g dist. water and 0.015 g ascorbic acid in 2 g dist. water. After the end temperature (ca. 100° C.) is reached, the gel is comminuted with a meat grinder and dried for 2 h at 150° C. in a circulating air oven. The dried product is coarsely ground, ground and the particles of size 150 to 850 μm sieved out for further conversion (powder F).

50 g powder F was mixed with vigorous stirring with a solution of 0.5 g ethylene carbonate and 1.5 g water and then heated for 40 minutes in an oven regulated to 160° C.

TABLE

| Number | measurement | Delay period* |
| --- | --- | --- |
| 1 | zero value (without SAP) | 2 h |
| 2 | Example 1 | 14 h |
| 3 | Example 2 | 7.5 h |
| 4 | Comparative example 1 | 5 h |
| 5 | Comparative example 2 | 3 h |
| 6 | Example 3 | 9 h |
| 7 | Comparative example 3 | 5 h |

*Delay period of the bacterial decomposition activity up to an $NH_3$ liberation of >200 ppm × h.

It is seen from the table that through the addition of small quantities of silver salt a clear bacteriostatic effect is achieved. Superabsorbers of this type are therefore extremely well suited for odor control when used, for example, in incontinence articles. It is furthermore clear that silver-free superabsorbers can clearly delay ammonia formation.

It is also seen from comparative example 1 that a substantially insoluble silver salt such as silver chloride does not achieve the effectiveness of silver nitrate.

Examples 2 and 3 further show that even with water-absorbing polymer particles comprising silver salts and reduced degree of neutralization, a clear bacteriostatic effect is achieved, which makes it possible to achieve an effective retardation of ammonia liberation with very low silver concentrations.

The invention claimed is:

1. A water-absorbing, antimicrobial polymer particle comprising:
   from about 1 to about 500 ppm, based on the polymer particle, of a silver ion based on a silver salt $Ag_mX_n$, wherein the silver salt has a solubility product of at least about $1\times10^{-8}(mol/l)^{m+n}$;
   at least about 10 wt. %, based on the polymer particle, of a water-absorbing polymer based on:
   ($\alpha$1) from about 50 to about 99.99 wt. % of acrylic acid which is neutralized to at least 25 mol. %,
   ($\alpha$2) from 0 to about 40 wt. % polymerized, monoethylenically unsaturated monomers polymerizable with $\alpha$1,
   ($\alpha$3) from about 0.01 to about 5 wt. % of one or more crosslinkers,
   ($\alpha$4) from 0 to about 30 wt. % of a water soluble polymer as well as
   ($\alpha$5) from 0 to about 20 wt. % of one or more auxiliaries, wherein the sum of the weight quantities ($\alpha$1) to ($\alpha$5) amounts to 100 wt. %;
   wherein the concentration of the silver ion based on a silver salt in at most about 90 vol. % of the water-absorbing, antimicrobial polymer particle is less than about 0.01 ppm and
   wherein the water-absorbing, antimicrobial polymer particle is post-crosslinked with a post-crosslinker in a quantity within a range of from about 0.01 to about 30 wt. %, based on the weight of the polymer particle.

2. The water-absorbing, antimicrobial polymer particle comprising:
   from about 1 to about 500 ppm, based on the polymer particle, of a silver ion based on a silver salt $Ag_mX_n$, wherein the silver salt has a solubility product of at least about $1\times10^{-8}(mol/l)^{m+n}$;
   at least about 10 wt. %, based on the polymer particle, of a water-absorbing polymer based on:
   ($\alpha$1) from about 50 to 99.99 wt. % of acrylic acid which is neutralized to at least 25 mol. %,
   ($\alpha$2) from 0 to about 40 wt. % polymerized, monoethylenically unsaturated monomers polymerizable with $\alpha$1,
   ($\alpha$3) from about 0.01 to about 5 wt. % of one or more crosslinkers,
   ($\alpha$4) from 0 to about 30 wt. % of a water soluble polymer as well as
   ($\alpha$5) from 0 to about 20 wt. % of one or more auxiliaries, wherein the sum of the weight quantities ($\alpha$1) to ($\alpha$5) amounts to 100 wt. %;
   wherein the concentration of the silver ion based on a silver salt in no volume part of the water-absorbing, antimicrobial polymer particle is less than about 0.01 ppm and
   wherein the water-absorbing, antimicrobial polymer particle is post-crosslinked with a post-crosslinker in a quantity within a range of from about 0.01 to about 30 wt. %, based on the weight of the polymer particle.

3. The water-absorbing, antimicrobial polymer particle comprising:
   from about 1 to about 500 ppm, based on the polymer particle, of a silver ion based on a silver salt $Ag_mX_n$, wherein the silver salt has a solubility product of at least about $1\times10^{-8}(mol/l)^{m+n}$; at least about 10 wt. %, based on the polymer particle, of a water-absorbing polymer based on:
   ($\alpha$1) from about 50 to about 99.99 wt. % of acrylic acid which is neutralized to at least 25 mol. %,
   ($\alpha$2) from 0 to about 40 wt. % polymerized, monoethylenically unsaturated monomers polymerizable with $\alpha$1,
   ($\alpha$3) from about 0.01 to about 5 wt. % of one or more crosslinkers,
   ($\alpha$4) from 0 to about 30 wt. % of a water soluble polymer as well as
   ($\alpha$5) from 0 to about 20 wt. % of one or more auxiliaries, wherein the sum of the weight quantities ($\alpha$1) to ($\alpha$5) amounts to 100 wt. %;
   wherein the concentration of the silver ion based on a silver salt in at most about 90 % of the water-absorbing, antimicrobial polymer particle is less than about 0.01 ppm and
   wherein the pH value of the water-absorbing, antimicrobial polymer particle lies within a range from about 4.5 to about 7.

4. The water-absorbing, antimicrobial polymer particle comprising:
   from about 1 to about 500 ppm, based on the polymer particle, of a silver ion based on a silver salt $Ag_mX_n$, wherein the silver salt has a solubility product of at least about $1\times10^{-8}(mol/l)^{m+n}$;
   at least about 10 wt. %, based on the polymer particle, of a water-absorbing polymer based on:
   ($\alpha$1) from about 50 to about 99.99 wt. % of acrylic acid which is neutralized to at least 25 mol. %,
   ($\alpha$2) from 0 to about 40 wt. % polymerized, monoethylenically unsaturated monomers polymerizable with $\alpha$1,
   ($\alpha$3) from about 0.01 to about 5 wt. % of one or more crosslinkers,
   ($\alpha$4) from 0 to about 30 wt. % of a water soluble polymer as well as
   ($\alpha$5) from 0 to about 20 wt. % of one or more auxiliaries, wherein the sum of the weight quantities ($\alpha$1) to ($\alpha$5) amounts to 100 wt. %;
   wherein the concentration of the silver ion based on a silver salt in no volume part of the water-absorbing, antimicrobial polymer particle is less than about 0.01 ppm and
   wherein the pH value of the water-absorbing, antimicrobial polymer particle lies within a range of from about 4.5 to about 7.

5. A process for producing a water-absorbing, antimicrobial polymer particle, whereby as reagents
   ($\beta$1) from 55 to about 99.99 wt. % of acrylic acid which is neutralized to at least 25 mol. %,
   ($\beta$2) from 0 to about 40 wt. % of polymerized, monoethylenically unsaturated monomers polymerizable with $\beta$1,
   ($\beta$3) from about 0.01 to about 5 wt. % of one or more crosslinkers,
   ($\beta$4) from 0 to about 30 wt. % of a water soluble polymer as well as
   ($\beta$5) from 0 to about 20 wt. % of one or more auxiliaries, wherein the sum of the weight quantities ($\beta$1) to ($\beta$5) amounts to 100 wt. % are polymerized together with formation of a water-absorbing polymer;

wherein from about 1 to about 500 ppm of a silver ion in the form of a water soluble silver salt $Ag_mX_n$ with a solubility product of at least about $1\times10^{-8}(mol/l)^{m+n}$ dissolved in a solvent, based on the reagents, is added to the reagents before the end of the formation of the water-absorbing polymer, and wherein the water-absorbing polymer is comminuted, dried and optionally ground and is post-crosslinked in a post-crosslinking step with a post-crosslinker in a quantity within a range of from about 0.01 to about 30 wt. %, based on the as yet untreated polymer.

6. The process for producing a water-absorbing, antimicrobial polymer particle, whereby as reagents ($\beta$1) from 50 to about 99.99 wt. % of acrylic acid which is neutralized to at least 25 mol. %, ($\beta$2) from 0 to about 40 wt. % of polymerized, monoethylenically unsaturated monomers polymerizable with $\beta$1, ($\beta$3) from about 0.01 to about 5 wt. % of one or more crosslinkers, ($\beta$4) from 0 to about 30 wt. % of a water soluble polymer as well as ($\beta$5) from 0 to about 20 wt. % of one or more auxiliaries,
wherein the sum of the weight quantities ($\beta$1) to ($\beta$5) amounts to 100 wt. %, are polymerized together with formation of a water-absorbing polymer;

wherein from about 1 to about 500 ppm of a silver ion in the form of a water soluble silver salt $Ag_mX_n$ with a solubility product of at least about $1\times10^{-8}$ $(mol/l)^{m+n}$ dissolved in a solvent, based on the reagents, is added to the reagents before the end of the formation of the water-absorbing polymer, and wherein the ethylenically unsaturated, acid groups-containing monomers ($\beta$1) are neutralized such that the pH value of the water-absorbing polymer particle lies within the range of from about 4.5 to about 7.

7. The process for producing a water-absorbing, antimicrobial polymer particle, whereby as reagents ($\beta$1) from 55 to about 99.99 wt. % of acrylic acid which is neutralized to at least 25 mol. %, ($\beta$2) from 0 to about 40 wt. % of polymerized, monoethylenically unsaturated monomers polymerizable with $\beta$1, ($\beta$3) from about 0.01 to about 5 wt. % of one or more crosslinkers, ($\beta$4) from 0 to about 30 wt. % of a water soluble polymer as well as ($\beta$5) from 0 to about 20 wt. % of one or more auxiliaries,
wherein the sum of the weight quantities ($\beta$1) to ($\beta$5) amounts to 100 wt. % are polymerized together with formation of a water-absorbing polymer;

wherein from about 1 to about 500 ppm of a silver ion in the form of a water soluble silver salt $Ag_mX_n$ with a solubility product of at least about $1\times10^{-8}$ $(mol/l)^{m+n}$ dissolved in a solvent, based on the reagents, is added to the reagents before the end of the formation of the water-absorbing polymer, and wherein the water-absorbing polymer is comminuted, dried and optionally ground and is post-crosslinked in a post-crosslinking step with a post-crosslinker in a quantity within a range of from about 0.01 to about 30 wt. %, based on the as yet untreated polymer.

8. The water-absorbing anti-microbial polymer particle of claim 1 wherein from about 50 to about 80 mol % of the acid groups of the acrylic acid are neutralized with an alkali or alkaline earth salt.

9. The water-absorbing anti-microbial polymer particle of claim 1 wherein the silver salt is silver nitrate.

10. The water-absorbing anti-microbial polymer particle of claim 1 further comprising at least one of the following properties:

(A) the maximum absorption of about 0.9 wt. % NaCl solution according to ERT 440.1-99 lies within a range of from at least about 10 to about 1000 g/g;

(B) the part extractable with about 0.9 wt. % aqueous NaCl solution according to ERT 470.1-99 amounts to less than about 30 wt. %, respectively based on the polymer;

(C) the bulk density according to ERT 460.1-99 lies within the range of from about 300 to about 1000 g/l;

(D) the pH value of about 1 g of the polymer in about 11 water according to ERT 400.1-99 lies within the range of from about 4 to about 10;

(E) the Centrifugation Retention Capacity (CRC) according to ERT 441.1-99 lies within the range of from about 10 to about 100 g/g.

11. Fibers, films, foams or formed bodies, comprising the polymer particle of claim 1.

12. A composite comprising the polymer particle according to claim 1 and a substrate.

13. A hygiene article, for prevention or treatment of skin irritations caused by body excretions comprising the polymer particle according to claim 1.

* * * * *

UNITED STATES PATENT AND TRADEMARK OFFICE
CERTIFICATE OF CORRECTION

PATENT NO. : 7,625,957 B2
APPLICATION NO. : 10/512351
DATED : December 1, 2009
INVENTOR(S) : Jörg Harren et al.

It is certified that error appears in the above-identified patent and that said Letters Patent is hereby corrected as shown below:

Column 4
Line 5, "$1\times10^{-5}(mol/l)_{m+n}$" should read -- $1\times10^{-5}(mol/l)^{m+n}$ --.

Column 6
Line 13, "in quatemated form" should read -- in quaternated form --.

Column 8
Line 7, "particularly 20 preferably" should read -- particularly preferably --.
Line 32, "$1\times10^{-3}(mol/l)_{m+n}$" should read -- $1\times10^{-3}(mol/l)^{m+n}$ --.

Column 11
Line 35, "$1\times10^{-6}(mol/l)_{m+n}$" should read -- $1\times10^{-6}(mol/l)^{m+n}$ --.
Line 36, "$1\times10^{-5}(mol/l)_{m+n}$" should read -- $1\times10^{-5}(mol/l)^{m+n}$ --.
Line 43, "about Ig," should read -- about 1g --.

Column 12
Line 25, "of Ig of" should read -- of 1g of --.

Column 18
Line 20, "about 90 %" should read -- about 90 vol. % --.
Line 29, "salt $Ag_mX_n$-" should read -- salt $Ag_mX_n$, --.

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

PATENT NO. : 7,625,957 B2
APPLICATION NO. : 10/512351
DATED : December 1, 2009
INVENTOR(S) : Harren et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 824 days.

Signed and Sealed this

Second Day of November, 2010

David J. Kappos
*Director of the United States Patent and Trademark Office*